(12) United States Patent
Lorenz

(10) Patent No.: US 10,450,558 B2
(45) Date of Patent: Oct. 22, 2019

(54) METHOD FOR ISOLATING MICROBIAL DNA

(71) Applicant: Molzym GmbH & Co. KG, Bremen (DE)

(72) Inventor: Michael Lorenz, Bad Zwischenahn (DE)

(73) Assignee: Molzym GmbH & Co. KG, Bremen (DE)

( * ) Notice: Subject to any disclaimer, the term of this patent is extended or adjusted under 35 U.S.C. 154(b) by 210 days.

(21) Appl. No.: 15/309,580

(22) PCT Filed: May 7, 2015

(86) PCT No.: PCT/EP2015/060130
§ 371 (c)(1),
(2) Date: Nov. 8, 2016

(87) PCT Pub. No.: WO2015/169933
PCT Pub. Date: Nov. 12, 2015

(65) Prior Publication Data
US 2017/0152510 A1    Jun. 1, 2017

(30) Foreign Application Priority Data
May 9, 2014    (EP) .................................. 14167811

(51) Int. Cl.
*C12N 15/10*    (2006.01)
(52) U.S. Cl.
CPC ................................ *C12N 15/1017* (2013.01)
(58) Field of Classification Search
CPC .................................................. C12N 15/1017
USPC ....................................................... 536/25.4
See application file for complete search history.

(56) References Cited

U.S. PATENT DOCUMENTS

| 2010/0240023 | A1 | 9/2010 | Hermet et al. |
| 2017/0044483 | A1 | 2/2017 | Faltin et al. |

FOREIGN PATENT DOCUMENTS

| DE | 102005009479 | 9/2006 |
| EP | 1861495 | 12/2007 |
| EP | 2333105 | 6/2011 |
| EP | 2942394 | 11/2015 |
| JP | 2012019723 | 2/2012 |
| WO | 03/070898 A2 | 8/2003 |
| WO | 03/070898 A3 | 8/2003 |
| WO | 2012/002887 | 1/2012 |
| WO | 2015169933 | 11/2015 |

OTHER PUBLICATIONS

International Search Report in corresponding PCT Application Serial No. PCT/EP2015/060130, dated Jul. 9, 2015, 7 pages.
O'Mahony, et al., "Integration of bacteria capture via filtration and in situ lysis for recovery of plasmid DNA under industry compatible conditions," Biotechnol. Prog., vol. 23, issue 4, Aug. 3, 2007, pp. 895-903.
"SepsiTest™ Pathogen DNA Extraction and PCR Analysis Version 3.0," http://www.goffinmoleculartechnologies.com/wp-content/uploads/2014/01/SepsiTest_V3-0_IVD_CE.pdf, Oct. 2013, 40 pages.
International Extended Search Report in corresponding PCT Application Serial No. PCT/EP2015/060130, dated Feb. 19, 2015, 10 pages.
International Partial Search Report in corresponding European Application Serial No. 14167811.0, dated Oct. 27, 2014, 7 pages.
International Preliminary Report on Patentability in corresponding PCT Application Serial No. PCT/EP2015/060130, dated Nov. 15, 2016, 9 pages.

*Primary Examiner* — Jezia Riley
(74) *Attorney, Agent, or Firm* — Hovey Williams LLP

(57) ABSTRACT

The present invention relates to a new method for enriching and/or isolating nucleic acids from microbial cells which comprises filtering a liquid sample through a nucleic acid-binding matrix which has a pore size small enough to retain microbial cells, lysing the microbial cells on the matrix to release the nucleic acids from the microbial cells, binding the nucleic acids to the matrix and subsequently eluting the DNA. The invention also relates to a method for enriching and/or isolating nucleic acids from microbial cells which are present in a liquid sample that comprises microbial cells and higher eukaryotic cells and/or tissues. The invention also provides a cartridge for carrying out the methods of the invention. Finally, the invention relates to kits for carrying out the methods of the invention.

15 Claims, 4 Drawing Sheets

METHOD FOR ISOLATING MICROBIAL DNA

RELATED APPLICATIONS

This application is the National Stage of International Patent Application No. PCT/EP2015/060130, filed May 7, 2015, which is hereby incorporated by reference in its entirety, and which claims priority to European Patent Application No. 14167811.0, filed May 9, 2014.

The present invention relates to a new method for enriching and/or isolating nucleic acids from microbial cells which comprises filtering a liquid sample through a nucleic acid-binding matrix which has a pore size small enough to retain microbial cells, lysing the microbial cells on the matrix to release the nucleic acids from the microbial cells, binding the nucleic acids to the matrix and subsequently eluting the DNA. The invention also relates to a method for enriching and/or isolating nucleic acids from microbial cells which are present in a liquid sample that comprises microbial cells and higher eukaryotic cells and/or tissues. The invention also provides a cartridge for carrying out the method of the invention. Finally, the invention relates to kits for carrying out the method of the invention.

BACKGROUND OF THE INVENTION

The isolation and purification of microbial, and in particular bacterial, nucleic acids from biological samples has become a routine tool in different fields of techniques. For example, the isolation of bacterial DNA in human blood samples is routinely performed during the screening of blood products for bacterial contaminations to prevent transfusion-transmitted diseases.

A common approach for the isolation of bacterial DNA from human blood samples involves the processing of the sample to release the DNA from whole cells or tissue extracts followed by DNA purification in spin columns or via magnetic beads. A number of DNA purification kits are commercially available and can be used for this purpose. However, these approaches have the drawback that the DNA from human blood cells is present in the sample in large amounts and might interfere with the detection of the microbial DNA. More sophisticated methods make use of immobilized proteins with ligands that bind to methylated human DNA to separate this DNA from the bacterial DNA that is present in the same sample (immuPREP Bacteria DNA Kit, Jena Analytik).

Methods for the consecutive lysis of blood cells and microbial cells are also known. EP 1 861 495 describes a method in which in a first step a chaotropic buffer is used to lyse human blood cells, but not microbial cells which are present in the same sample. The DNA released from the blood cells is degraded by the addition of a nuclease. Subsequently, the microbial cells are concentrated and the DNA is extracted and purified.

Although the above methods have provided a considerable contribution, there is still a need to develop new methods that allow for enriching and/or isolating nucleic acids from microbial cells, in particular from mixed samples which contain both microbial and higher eukaryotic cells or tissues, which are less laborious than those commonly known in the prior art. The method should preferably include fewer steps that require the manual intervention of the operator. Even more preferably, the method should be amenable to automation and require less time than currently used methods. The method of the present invention fulfills these needs and provides additional advantages as well.

It has unexpectedly been found by the inventors that microbial cells entrapped by filtration in a matrix can be efficiently lysed on this matrix, such as a commonly known silica or glass matrix which is part of a spin column, for DNA purification, without losing considerable amounts of DNA during cell lysis. Specifically, it was noted that, although the conditions during cell lysis are unfavorable for DNA binding, the DNA released from the cells was not washed out, but instead maintained on the filter matrix and could be reversibly bound to the matrix by the addition of monovalent and/or multivalent cations, e.g. magnesium or calcium cations, or cations from a chaotropic salt such as guanidine hydrochloride. Unbound material can be removed from the filter matrix by washing the matrix with a suitable washing buffer. Finally, the microbial DNA is eluted from the matrix in high purity. Without wishing to be bound by theory, it is assumed that the DNA is released from the microbial cells in a gentle way so that it maintains its highly complex molecular structure which enables it to remain loosely associated with the filter matrix even in the absence of high concentrations of monovalent or multivalent cations. This insight allows for an improved method that includes cell lysis directly on the filter matrix.

Compared to the common centrifugation-based methods, the method of the invention takes only half the time. Moreover, the method of the invention is amenable to automation, which requires only a vacuum station and an automated pipetting system, thereby making automation less expensive compared to centrifugation-based methods.

DESCRIPTION OF THE INVENTION

Figure 1:
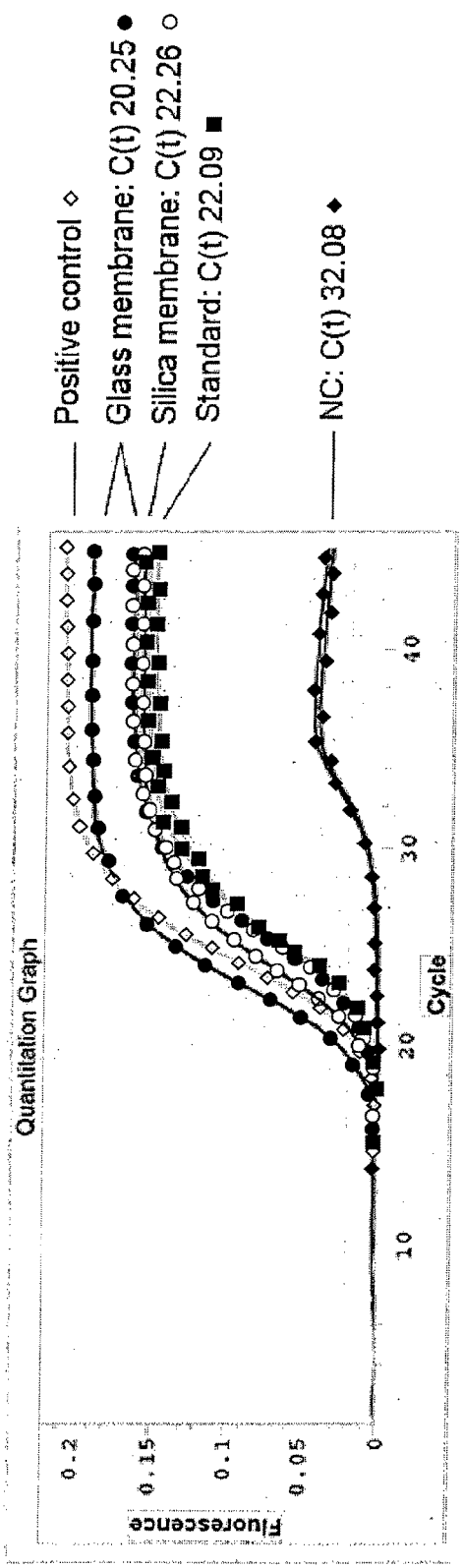
FIG. 1 shows the extraction of immobilized *S. aureus* ($6.8 \times 10^4$ cfu/mL) by the method of the invention. DNA was measured in a quantitative Real-Time PCR assay (Molzym Mastermix 16S). Standard: centrifugation method (Molzym MolYsis Complete5).

In a first aspect, the invention relates to a method for enriching and/or isolating nucleic acids from microbial cells that are present in a liquid sample. The method comprises the following steps:

(a) filtering a liquid sample comprising microbial cells through a nucleic-acid binding matrix, preferably a negatively charged filter material such as silica or glass, which has a pore size small enough to retain the microbial cells;
(b) lysing the microbial cells on the matrix to release the nucleic acids from the microbial cells;
(c) optionally, degrading proteins on the matrix by addition of an enzyme having proteinase activity;
(d) binding the nucleic acids to the matrix by addition of monovalent and/or multivalent cations;
(e) optionally, washing the matrix to remove any unbound material; and
(f) eluting the nucleic acids.

The method of the invention is useful for enriching and/or isolating nucleic acids from microbial cells. The objective of the method described below is to provide the microbial nucleic acids in substantially pure form, i.e. separated from most other components such as proteins, lipids, cell wall components and the like. It is preferred that the nucleic acids eluted in the terminal step of the method are at least 50% pure, preferably at least 60%, at least 70%, at least 80%, at least 90%, at least 95%, at least 96%, at least 97%, at least 98%, or at least 99% pure.

In the context of the present invention, a nucleic acid is a single-stranded, double-stranded or partially double-stranded ribonucleic acid (RNA) or deoxyribonucleic acid (DNA) molecule. Moreover, the term comprises duplex and triplex structures that can be formed from DNA and/or RNA. According to a preferred embodiment of the invention, the nucleic acid to be enriched or isolated by the method of the invention is DNA, more preferably bacterial DNA.

As used herein, the terms "microbial cell" or "microorganism" denote a diverse group of organisms, which exist in nature autonomously as a single cell and hence differ from higher eukaryotic cells, in particular animal cells in a tissue, e.g. mammalian tissue cells, that do not occur in nature as a single cell, but exclusively in the form of multicellular organisms. The microbial cells are preferably prokaryotic cells, such as bacteria or archaebacteria, or also eukaryotic cells and cell associations like hyphae, such as yeasts, lower and higher fungi or protozoa. According to a preferred embodiment of the invention the microbial cells are prokaryotic cells. According to a particularly preferred embodiment the prokaryotic cells are bacteria.

The method of the invention can be used for enriching or isolating nucleic acid from all different genera of Gram-positive and Gram-negative bacteria, for example, from bacteria of the genera *Mycobacterium, Enterococcus, Streptococcus, Staphylococcus, Salmonella, Legionella, Clamydia, Shigella, Pseudomonas, Listeria, Yersinia, Corynebacterium, Bordetella, Bacillus, Clostridium, Haemophilus, Helicobacter* and *Vibrio*.

The method of the invention can also be applied for enriching or isolating nucleic acid from different types of fungi, e.g. those of the genera *Aspergillus* (e.g. *A. fumigatus, A. niger, A. flavus, A. nidulans*), *Basidiobolus* (e.g. *B. microsporus, B. ranarum*), *Cephalosporium* (e.g. *C. chrysogenum, C. coremioides, C. diospyri, C. gregatum*) and other pathogenic fungi of the genera *Entomophthora, Skopulariopsis, Mucor, Rhizomucor, Absidia, Rhizopus, Altenaria, Stemphylium, Botrytis, Chrysosporium, Curvularia, Helmithosporium, Hemispora, Nigrospora, Paecilomyces, Phoma, Thielavia* or *Syncephalastrum*. Pathogenic yeasts of the genus *Candida*, e.g. *C. albicans, C. guilliermondii, C. kruzei, C. parapsilosis, C. tropicalis* and others are also covered by the invention. In addition, the microbial cells to be used in the method of the invention can also comprise algae, for example, *Ceratium massiliense, Dinophysis nitra, Gymnodinium sanguineum, Trachelomonas* spp., *Euglena* spp., *Coscinodiscus* spp., *Eremosphaera, Chlorella* or *Chlorococcum*.

Although the invention is not limited in this way, it is particularly preferred that the method of the invention is directed to the enrichment or isolation of bacterial DNA.

The above-described method of the invention comprises a first step in which a liquid sample with the microbial cells is filtered through a filter matrix, preferably a filter membrane, which is capable of binding nucleic acids, in particular DNA and/or RNA. The matrix can comprise or consist of any material which is known in the art to be capable of reversibly binding nucleic acids, such as DNA, and which contains or can be modified to contain pores that retain microbial cells. Preferably, the matrix used for filtration comprises or consists of a charged or partially charged filter material, such as a charged organic polymer. The positive or negative charge can originate either from ionic charges or from electric dipoles. Positively charged filter materials include, e.g. polyvinlidene fluoride and nylon. It is particularly preferred that the filter matrix used in the method of the invention is negatively charged or partially negatively charged. Such materials include glass, e.g. in the form of glass powder, silica, cellulose acetate, cellulose triacetate, regenerated cellulose (RC), cellulose nitrate, polyethersulfone (PES) or polycarbonate materials. In one embodiment, the matrix for use in the method of the invention is a silica material, preferably a silica gel. In another preferred embodiment, the matrix for use in the method of the invention is a filter membrane, preferably a cellulose acetate, cellulose nitrate, PES or polycarbonate membrane. In a preferred embodiment of the invention, the matrix for use in the method of the invention is not a nylon membrane.

The matrix is further characterized by the possession of pores which have a size suitable for filtration. These pores are sufficiently small to retain microbial cells, in particular bacterial cells, i.e. the microbial cells are collected on the filter matrix upon filtration of the liquid sample while the liquid and all components dissolved therein pass through the filter matrix. For effectively retaining microbial cells, it is preferred that the median pore size of the filter matrix is less than 4 μm, less than 3 μm, less than 2 μm, less than 1 μm, less than 0.5 μm, or less than 0.25 μm. Commonly used filter materials used for sterile filtration in the pharmaceutical and food industry have a pore size of 0.22 μm. Accordingly, a pore size of 0.22 μm or below, such as 0.2 μm, can also be used in the method of the invention. Methods for preparing different types of matrices, such as silica matrices, with a defined pore size are well known in the art. In addition, commercially available filter materials obtainable from manufacturers such as Qiagen, Sartorius and Millipore can also conveniently be used in the method of the present invention.

In a particularly preferred embodiment, the matrix for use in the method of the invention is a silica or glass matrix having a median pore size in the range between 0.2-5 μm, more preferably between 0.2-2 μm, and even more preferably between 0.2-1 μm.

The liquid sample that is processed by the method of the invention has a viscosity which allows the sample to be passed through the filter matrix having the above-mentioned pore size. Where the viscosity of the sample is high and long filtration times are expected, it may be desirable to dilute the sample with water or a low concentrated Tris-HCl buffer. Where the sample contains tissue, such as mammalian tissue, the sample may need to be liquified before filtration.

For example, tissues can be liquified by treating them with a proteinase enzyme, such as proteinase K. For this purpose, the tissues are dissected in a buffer that contains proteinase K and incubated, e.g. for 10 minutes for 56° C.

In a simple embodiment of the invention, the filtration step can be carried out by gravity flow, i.e. the liquid sample is contacted with the filter matrix and the liquid is allowed to flow through the matrix by gravity. In a more preferred embodiment, the filtration step is performed by centrifugation, i.e. the liquid is passed through the matrix by applying a centrifugal force. For this purpose, the sample will normally be filtered using a spin column. In such an embodiment, the filter matrix will be integrated into a small column that can be placed into a collection tube, e.g. a 2 mL tube. Both the column and the collection tube are sized and shaped to fit into a standard centrifuge or microcentrifuge. Centrifugation of the column significantly accelerates filtration. In a particularly preferred embodiment of the invention, the filtration in step (a) will be accelerated by applying a reduced pressure on one side of the filter matrix, e.g. by using a vacuum device. For instance, stationary filtration columns can be used which are connected to a vacuum pump. Alternatively, where filtration is performed using a vacuum device, it is particularly preferred to use a cartridge as described below.

After completion of the initial filtration step, the microbial cells that were present in the liquid sample are located on the filter matrix. In the second step (b), the microbial cells are lysed on the matrix so as to release the nucleic acids from the cells, i.e. the nucleic acids become accessible to the filter matrix material. Depending on the microbial cells, lysis can be achieved in different ways. For example, if the method is directed to the isolation of bacterial nucleic acids, the cells can be lysed by the addition of a cell wall degrading enzyme, e.g. lysozyme or lysostaphine. If fungal cells or algae shall be processed with the methods of the invention, the cell wall degrading enzyme will be adapted accordingly. For example, fungal cells can be treated with chitinase or lyticase to degrade the cell wall. Other enzymes that may be used for disrupting the cells include mutanolysin, achromopeptidase, and proteinase K. The enzyme will normally be added to the filter matrix as a solution which is pipetted to the surface of the matrix so that the matrix is soaked with the solution. Where the method uses a vacuum device, it will be preferred to apply a short pulse of vacuum to soak the membrane with the liquid.

The solution used for effecting the lysis can contain, apart from the cell wall degrading enzyme, buffer components, such as TRIS or TRIS-HCL, in an amount of 0.01 to 0.1 mol/l, preferably 0.05 mol/l. The solution or buffer can also contain complexing agents like EDTA or citrate, which are useful for destabilizing the microbial cell wall, in an amount of 0.001 to 0.1 mol/l, preferably 0.01 mol/l. It is also preferred that the lysis solution or buffer contains a sugar, such as sucrose, in an amount of between 5-50% (wt/vol). A preferred lysis buffer of the invention is "buffer 3" which is referred to in the example part and to which a cell wall degrading enzyme such as lysozyme has to be added. According to a preferred aspect, the solution used for effecting the lysis of the cells that were present on the matrix contains between 0.01 to 0.1 mol/l TRIS-HCL at a pH of about 8.0, between 0.005 to 0.05 mol/l EDTA, and between 10-30% of a sugar such as sucrose. According to a more preferred aspect, the solution used for effecting the lysis of the cells that were present on the matrix contains 0.05 mol/l TRIS-HCL at a pH of about 8.0, 0.01 mol/l EDTA, and 20% sucrose. Suitable solutions or buffers for use in the method of the present invention can be prepared by a skilled person in accordance with common protocols.

Preferably, the lysis of the microbial cells in step (b) of the above method does not involve a precipitation of the nucleic acids which are released from the microbial cells. This means that the solution or buffer which is used for effecting lysis of the microbial cells does not contain compounds which would induce precipitation of nucleic acids, such as alcohols like ethanol or 2-propanol, high concentrations of urea or salts like NaCl, KCl, $NH_4Cl$ or LiCl. Preferably, the solution or buffer which is used for effecting lysis does also not contain multivalent cations such as $mg^{2+}$, $Ca^{2+}$, $Mn^{2+}$, $Al^{2+}$ and/or $Al^{3+}$.

The filter matrix will be incubated under conditions that allow the enzyme to degrade the microbial cell wall. The incubation condition will depend on different factors, e.g. the concentration of the enzyme in the solution that is added to the cells on the filter matrix. Generally, these conditions will include a temperature between 10-45° C., preferably between 20-45° C., more preferably 30-37° C., and an incubation time of 5-50 minutes, preferably 10-30 minutes. Incubation for 10-30 minutes at 20-25° C. or at 45° C. is particularly preferred.

Apart from cell wall degrading enzymes, chemical agents, e.g. oxidative compounds like sodium iodate, can be used for cell wall degradation for all types of microbial cells, e.g. bacterial and fungal cells.

According to the method of the invention, the nucleic acids which are released from the microbial cells are not precipitated during the step of cell lysis. Instead, the method of the invention encompasses cell lysis conditions which result in the nucleic acids, and in particular DNA, to remain soluble in the lysate. The soluble nucleic acids are retained on the matrix during the following steps of purification.

Optionally, the proteins which may be present on the filter matrix after cell lysis are degraded. For this, the matrix is contacted with an enzyme having proteinase activity under conditions that allow the enzyme to degrade the proteins released by lysis of the cells and any other non-microbial proteins that were present in the original sample. Normally, a solution containing the proteinase enzyme is brought to the filter matrix by pipetting so that the matrix is soaked with the solution. Where the method uses a vacuum device, it will again be preferred to apply a short pulse of vacuum to soak the membrane with the liquid. The filter matrix will then be incubated under conditions that allow the proteinase enzyme to degrade the proteins present on the matrix. The incubation conditions will once again depend on factors like the concentration of the proteinase enzyme that is added to the filter matrix. Generally, these conditions will include a temperature between 10-56° C., preferably between 20-56° C., more preferably 25-45° C., and an incubation time of 1-20 minutes, preferably 5-15 minutes. Incubation for 5-12 minutes, e.g. for 5-10 minutes at 20-25° C. or 45° C. is particularly preferred.

Where is method of the invention comprises a proteinase treatment, the order of steps (b) and (c) may be changed, i.e. step (b) can be carried out before or after step (c). Also, both steps can be performed simultaneously.

After degradation of the cell wall, release of the proteins from the microbial cells, and (optionally) degradation of the proteins, the nucleic acids which are still on the filter matrix are reversibly bound to the matrix by the addition of monovalent and/or multivalent cations. Preferably, multivalent cations are used for reversibly binding the nucleic acid to the filter matrix, preferably a glass or silica filter matrix. Multivalent cations that can be used for this purpose include $Mg^{2+}$, $Ca^{2+}$, $Mn^{2+}$, $Al^{2+}$ and/or $Al^{3+}$. The multivalent cations are preferably added in dissolved form as a solution, e.g. a solution of magnesium or calcium chloride. The concentration of the multivalent cations in the solutions which are used for binding the nucleic acids to the matrix can be between 0.2 and 0.02 mol/L, preferably between 0.1 and 0.04 mol/L, such as between 0.08 and 0.06 mol/L. The concentration of the multivalent cations in the solutions preferably is about 0.2 mol/L or less, 0.1 mol/L or less, e.g. 0.09 mol/L or less, 0.08 mol/L or less, 0.075 mol/L or less, 0.07 mol/L or less, 0.065 mol/L or less, 0.06 mol/L or less, 0.055 mol/L or less, 0.05 mol/L or less, 0.045 mol/L or less, 0.04 mol/L or less, 0.035 mol/L or less, 0.03 mol/L or less, 0.025 mol/L or less, 0.02 mol/L or less.

Monovalent cations that can be used for this purpose include $Na^+$, $K^+$, $NH_4^+$, and/or $Li^+$. Preferably, these monovalent cations are also added in dissolved form as a solution, e.g. as a sodium chloride or potassium chloride solution. The concentrations of the monovalent cations in the solutions which are used for binding the nucleic acids to the matrix are somewhat higher compared to the multivalent cations. Preferably, the concentrations of monovalent cations in these solutions are in the range of between 0.5 and 5 mol/L, preferably between 1 and 2.5 mol/L, such as between 1.5 and 2.0 mol/L. The concentration of the monovalent cations preferably is about 5 mol/L or less, e.g. 4 mol/L or less, 3.5 mol/L or less, 3 mol/L or less, 2.5 mol/L or less, 2 mol/L or less, 1.5 mol/L or less, 1 mol/L or less or 0.5 mol/L or less.

In one embodiment of the invention, the monovalent cations used for reversibly binding the nucleic acids to the matrix are derived from chaotropic agents, in particular chaotropic salts. Chaotropic agents are substances that disrupt regular molecular structures that are based on the formation of hydrogen bonds. Chaotropic agents destabilize the conformation of macromolecules by preventing formation of the $H_2O$ cage structures that are necessary for solvation. They display high affinity for water and therefore form a large hydration shell. Chaotropic agents, such as chaotropic salts, are well known to a person skilled in the art. The chaotropic salt from which the cations are derived is preferably selected from the group of the guanidine hydrochloride, sodium iodide, guanidine isothiocyanate or mixtures thereof. If the monovalent cations are derived from chaotropic salts, their concentration will be in the above range, e.g. between 0.5 and 5 mol/L, preferably between 1 and 2.5 mol/L, such as between 1.5 and 2.0 mol/L. The concentration of the monovalent cations of the chaotropic salt preferably is about 5 mol/L or less, e.g. 4 mol/L or less, 3.5 mol/L or less, 3 mol/L or less, 2.5 mol/L or less, 2 mol/L or less, 1.5 mol/L or less, 1 mol/L or less or 0.5 mol/L or less. The use of guanidine hydrochloride or guanidine isothiocyanate in these concentrations is particularly preferred.

Mixtures of both monovalent and multivalent cations in the concentration cited above can also be applied.

Optionally, the filter matrix is washed in a subsequent step to remove any unbound material, such as residual proteins or cell wall components. A suitable washing buffer for use in step (e) of the method of the invention comprises at least 50% (vol/vol) alcohol, more preferably at least 60%, at least 70%, at least 80%, at least 90%, or more alcohol. The alcohol preferably is ethanol.

In the final step of the method, the nucleic acids that have reversibly bound to the filter matrix are eluted to recover the nucleic acids. Elution can be achieved by contacting the filter matrix with a suitable volume of water or an aqueous buffer, such as TE buffer. For example, where columns with a volume of about 1 mL are used for filtration, the elution volume will be in the range of 10-500 µl, preferably between 100-250 µl, more preferably 200 µl. The elution of the nucleic acids by use of DNAse- and/or RNase-free water is particularly preferred. The filter matrix is soaked with the water or aqueous buffer and incubated for 1-5 minutes. Subsequently, the liquid is removed from the matrix, e.g. by filtration or by use of a vacuum.

The nucleic acids obtained as described above can be stored, e.g. at a temperature between −20° C. and −80° C. until further use or can be directly applied to downstream processing methods, such as PCR-based detection methods.

The filtration-based method of the invention can be used in a number of different technical fields. For example, the method of the invention is particularly relevant for monitoring water quality, preferably tab water quality. Since pathogenic bacteria, such as Enterobacteria, are normally present in tab water only in small numbers, the invention is particular advantageous, because it is based on filtration which allows the processing of high sample volumes. The method can also be applied for process control in the pharmaceutical industry to detect contamination of pharmaceutical products, such as medicinal products, with bacteria. Another field in which the method of the invention can be used is the detection of pathogenic bacteria in food items. Notably, the method is not restricted to the analysis of liquid food products; solid or semi-solid food items can be processed as well provided that they are liquefied in an initial step of the method.

The above method can advantageously be used for enriching and/or isolating nucleic acids from microbial cells which are present in a liquid sample that comprises both microbial cells and higher eukaryotic cells and/or tissues. The detection of nucleic acids, in particular DNA, from microbial cells which occur in composite samples together with higher eukaryotic cells or tissues often pose problems because the reliable detection of the microbial nucleic acids obtained from whole cell extracts is hampered by the excess of eukaryotic DNA which needs to be depleted in order to avoid false negative or positive results in molecular assays that target the microbial DNA. For example, the detection of DNA from pathogenic bacteria in blood is challenging due to the fact that there is a high excess of blood cell DNA and only small amounts of bacterial DNA. The filtration-based method of the present invention allows the initial separation of eukaryotic cells and/or tissues by selective lysis of the eukaryotic cells and/or tissues and a subsequent extraction of the microbial nucleic acids on the filter matrix. In this way, the selective enrichment or isolation of microbial nucleic acid from composite samples can be performed faster than with commonly available centrifugation-based methods.

Accordingly, in a second aspect, the invention also provides a method for enriching and/or isolating nucleic acids from microbial cells which are present in a liquid sample that comprises both microbial cells and higher eukaryotic cells and/or tissues, said method comprising:
(a) lysing the higher eukaryotic cells and/or tissues in the sample under conditions which do not result in the lysis of the microbial cells;
(b) degrading nucleic acids released from the higher eukaryotic cells and/or tissues by the addition of an enzyme having nuclease activity;
(c) optionally, degrading proteins by the addition of an enzyme having proteinase activity; and (d) subjecting the sample to the method according to the first aspect for enriching and/or isolating nucleic acids from microbial cells described above.

To this end, the present invention provides a method for the selective isolation of nucleic acid from microorganisms which are present in admixture with cells and/or tissues of eukaryotic origin.

The term "eukaryotic cell" or "eukaryote" denotes any cell of unicellular or multicellular organisms belonging to the phylogenetic group of the Eukarya. These cells possess a cell nucleus, which is enclosed by a cell membrane and comprises several DNA molecules, which divide by mitosis. Eukaryotic cells comprise single-celled organisms such as single-celled algae, fungi (e.g. yeasts) or protozoa, which can also live as parasites, commensals or saprophytes at times or permanently in or on a host organism. Furthermore, the cells of multicellular organisms, for example of animal organisms such as mammals, fungi or plants are also classified as eukaryotic cells.

The term "higher eukaryotic cell" refers to a eukaryotic cell of a higher state of development, such as those which occur in animal or plant organisms. On the one hand higher eukaryotic cells can be cells that are organized in a tissue, i.e. the higher eukaryotic cell does not perform all vital biochemical and metabolic functions independently, but as a rule is specialized for performing one or more functions. On the other hand the term also refers to single cells, such as blood cells or spermatozoa, e.g. those which occur in a liquor or an excreted product of a mammal (e.g. in blood, lymph, urine or saliva). "Higher eukaryotic tissue" refers to a collection of higher eukaryotic cells that are organized in a cell aggregate. Examples for higher eukaryotic tissues are tissues from organs of a mammal (e.g. from the liver, heart, skin, or pancreas). In a preferred embodiment, the higher eukaryotic cells and/or tissues are mammalian cells, more preferably human cells.

Mixed or composite samples comprising both higher eukaryotic cells and microbial cells are relevant in a number of technical applications. For example, the quality of cell cultures and blood products can be monitored by detecting DNA from contaminating bacteria. Apart from that, the method is useful for the diagnosis of pathogenic microorganisms in body fluids, such as blood, thrombocyte concentrates and erythrocyte concentrates, aspirates, cerebrospinal fluid and bronchio-alveolar lavage. Accordingly, the sample to be subjected to the method of the invention can comprise blood, a blood product, urine, feces, sputum, lavage, aspirate, wound smear, cerebrospinal fluid and bronchio-alveolar lavage, lymph and/or secretion of human or animal origin and/or tissues of human or animal origin or portions thereof.

In a particularly preferred embodiment, the sample is derived from a blood product, e.g. a thrombocyte or erythrocyte concentrate. In another preferred embodiment, the higher eukaryotic cells which are present together with the microbial cells in the liquid sample are blood cells or tissue cells of human or animal origin.

The method according to the second aspect of the invention starts with the lysis of the higher eukaryotic cells and/or tissues in the sample under conditions which do not result in the lysis of the microbial cells. According to a preferred embodiment of the present invention, lysis of the higher eukaryotic cells and/or tissues in the composite sample is carried out by adding a lysing agent. The lysing agent can be a chemical substance (or a mixture of substances) that disrupts the membrane and/or cell wall structure of cells or tissues. The conditions are selected in such a way that the lysing agent is first used at a concentration that leads to lysis of higher eukaryotic cells and tissues, so that the nucleic acids are released from them. The concentration of the particular agent is selected in such a way that the microbial cells (for example bacteria) contained in the same sample are not disrupted.

The lysing agent can for example be contained in a solution that is added to the sample before said sample is applied to the filter matrix. The solution can also contain other substances, which intensify and/or support the lysing action of the particular agents used. Preferably the lysing agents are contained in a buffered solution, which can comprise one or more buffers such as TRIS, MOPS or HEPES and/or chelating agents such as EDTA or EGTA.

According to a particularly preferred embodiment, the lysing agent comprises one or more chaotropic agents and/or one or more surfactants. The chaotropic agent used for lysis can be a chaotropic salt, for example guanidine hydrochloride, sodium iodide, guanidine isothiocyanate, sodium perchlorate, urea or mixtures thereof. The use of guanidine hydrochloride or guanidine isothiocyanate is particularly preferred. Guanidine salts can be used in concentrations up to 4-5 mol/L. Thus, the concentration of the chaotropic agent used for lysing the eukaryotic cells preferably is 5 mol/L or lower, such as 4 mol/L, 3.5 mol/L, 3 mol/L, 2.5 mol/L, 2 mol/L, 1.5 mol/L, 1 mol/L or 0.5 mol/L.

Surfactants can also be used for lysis of the eukaryotic cells. Surfactants are surface-active substances which concentrate preferentially at the interface of two media, e.g. at the water/air boundary. Anionic, cationic, amphoteric or nonionic surfactants can be used according to the invention. Anionic surfactants have a negative charge of the molecule and comprise e.g. alkylbenzene sulfonates and alkane sulfonates. Cationic surfactants bear a positive charge and comprise e.g. distearyl dimethylammonium chloride. Nonionic surfactants have no charge and comprise fatty alcohol ethoxylates and alkyl polyglucosides. Amphoteric surfactants carry both a positive and a negative charge and comprise for example betaines. Concentrations of up to 20% (wt/wt) can be applied in the method of the invention without affecting the integrity of the microbial cells in the sample. Non-limiting examples that can be used in the method of the invention include sodium dodecyl sulfate, Brij40, Triton X-100, and/or Tween-20.

Lysis of the eukaryotic cells should be performed under conditions that ensure that at least a considerable proportion of the higher eukaryotic cells and/or tissues in the sample are lysed. More preferably, substantially all higher eukaryotic cells and/or tissues in the sample are lysed. The conditions should be selected such that more than 30% of the higher eukaryotic cells and/or tissues contained in the sample are lysed, and preferably more than 40%, 50%, 60%, 70%, 80%, 90%, 95% or 99% of the higher eukaryotic cells and/or tissues in the sample.

In order to determine the proportion of higher eukaryotic cells and/or tissues that are lysed under the selected conditions, quantitative control tests can be carried out which provide information regarding the lysis of the cells. The extent of lysis of the higher eukaryotic cells and/or tissues can, for example, be determined using a quantitative PCR reaction. For this purpose, an aliquot from the sample which was not subjected to lysis/DNAse treatment is analyzed in parallel with a second aliquot from the same sample which has been subjected to lysis/DNAse treatment.

The conditions selected for lysis of the eukaryotic cells will preferably not or not significantly affect the integrity of the microbial cells in the sample. It is preferred that these conditions result in the lysis of 30% or less of the microbial cells in the sample. Preferably, the conditions are selected to lyse less than 25%, 20%, 15%, 10%, or 5%, wherein less than 3% or less than 1% is particularly preferred. The degree of microbial cell lysis can be determined by measuring the optical density at a wavelength of 260 nm. At this wavelength, nucleic acids display a characteristic absorption maximum so that the lysis of the cells can be quantified on the basis of the release of nucleic acids. Alternatively, PCR techniques can also be used for quantification.

The initial lysis of the eukaryotic cells will be performed in a separate tube in order to avoid binding of the DNA released from the eukaryotic cells to the matrix, e.g. the glass or silica filter, in the presence of the chaotropic agent. Only after degradation of the DNA from higher eukaryotes and, optionally, the proteins is the sample transferred to the filter matrix.

In a subsequent step, the nucleic acids released from the eukaryotic cells and/or tissues are degraded by the addition of an enzyme having nuclease activity. Such an enzyme effects hydrolytic cleavage of the ester bond between the 5'-phosphate group of a nucleotide and the 3'-hydroxyl group of the adjacent nucleotide in a nucleic acid and therefore accomplishes the degradation of a DNA or RNA molecule. Nucleases are known from numerous organisms and cleave either RNA or DNA molecules to smaller units or even to their monomers. In a preferred embodiment, the nuclease used is a DNA-degrading nuclease, i.e. a nuclease that is able to cleave single-stranded, double-stranded and partially double-stranded DNA molecules into smaller units or monomers. Such enzymes are also termed "DNAses" in the state of the art.

The nuclease or DNA-degrading nuclease can be an endonuclease or an exonuclease. While exonucleases degrade a nucleic acid chain starting from one or from both ends of the chain, the degradation of a nucleic acid chain mediated by endonucleases starts from a position within the chain. It is preferred that the nuclease used in the method of the invention for degrading the eukaryotic nucleic acid is an endonuclease.

According to an even more preferred embodiment, the nuclease for use in step (b) of the above method for the degradation of nucleic acids released from the eukaryotic cells is one of the endonuclease I molecules disclosed in EP 1 861 495 as SEQ ID NOs:1-4. These bacterial endonuclease I enzymes have the particular advantage that they were found to maintain their activity under chaotropic conditions, i.e. in the presence of a chaotropic agent and/or surfactant. Hence, where the lysis of eukaryotic cells is effected by the addition of a chaotropic agent, such as a chaotropic salt, there is no need for a laborious and time-consuming removal of the lysis buffer before contacting the sample with the nuclease. Instead, the endonuclease can be part of the lysis buffer, but it can also be added to such buffer during lysis of the eukaryotic cell, e.g. 5-10 minutes after addition of the lysis buffer. In a preferred embodiment, the nuclease is the endonuclease I from Escherichia coli having the sequence of SEQ ID NO:1 of EP 1 861 495.

If the method of the invention makes use of a nuclease that is stable under chaotropic conditions, it is preferred that the total concentration of the chaotropic agents in the reaction is from 0.1 mol/L to 2.5 mol/L, wherein a range of 0.5 mol/L to 2 mol/L and a range of 1 mol/L to 1.5 mol/L is particularly preferred. This means that the concentration of a chaotropic salt such as guanidine hydrochloride or guanidine isothiocyanate can be 0.1 mol/L, 0.5 mol/L, 1 mol/L, 1.5 mol/L, 2 mol/L or 2.5 mol/L, provided that such salt is used as the only chaotropic substance in the reaction batch.

If mixtures of more than one chaotropic agent are used, e.g. mixtures of guanidine hydrochloride and guanidine isothiocyanate, the total concentration of chaotropic agents should fall within the above ranges.

Similarly, when using a nuclease which exhibits stability under chaotropic conditions, the total amount of surfactant is preferably 2% (wt/wt) of the total mixture or less. According to a preferred embodiment the total amount of surfactant in the reaction batch is between 0.1-2%, wherein amounts of 0.5-1.5% and 1.2-1.4% are particularly preferred. A person skilled in the art will have no problems to determine the optimum for each lysing buffer by conducting simple activity tests in the presence of different combinations of salts and surfactants.

The sample to which the lysing agent has been added is subsequently incubated under conditions that allow the nuclease enzyme to degrade the nucleic acids, in particular DNA, released from the eukaryotic cells. While the optimum conditions that provide for the rapid and complete degradation of nucleic acids will depend on different factors, e.g. the concentration of the nuclease enzyme that is added to the sample, the sample volume and the like, suitable conditions will generally include a temperature between 10-50° C., preferably between 20-45° C. and an incubation time of 5-20 minutes, preferably 10-15 minutes. Incubation for 10-12 minutes at 45° C. is particularly preferred.

Optionally, proteins released from the eukaryotic cells and any other proteins that might be in the sample, e.g. serum proteins, are degraded by the addition of a proteinase enzyme. The proteinase treatment can be carried out as described above. Preferably, the enzyme having proteinase activity is proteinase K which is used at a temperature of between 10-56° C., more preferably 20-56° C. for 10-30 min, e.g. for 10 min at 45° C.

The present invention provides a kit for carrying out the method of the first aspect of the invention. The kit will comprise buffers and reagents that are suitable for the isolation and/or purification of microbial nucleic acids, in particular microbial DNA. The kit will include a suitable matrix, preferably a glass or silica matrix, suitable for binding of nucleic acids, in particular DNA. The matrix is preferably integrated into a small spin column, e.g. having a capacity of between 0.5-2 mL, preferably 0.8 mL, or a stationary column, e.g. having a capacity of 1-10 mL. The kit will further comprise reagents, e.g. at least one cell wall degrading enzyme such as lysozyme. Also included is at least one enzyme having proteinase activity, such as proteinase K. Finally, the kit will include at least one chaotropic agent, such as a chaotropic salt, and/or at least one monovalent or multivalent cation, such as magnesium chloride, for binding nucleic acid to the filter matrix.

The present invention also provides a kit for carrying out the method of the second aspect of the invention. The kit will generally comprise the above-mentioned buffers and reagents for the isolation and/or purification of microbial nucleic acids, in particular microbial DNA. In addition, a kit for carrying out the method of the second aspect of the invention will include at least one DNA-degrading nuclease, such as an endonuclease I enzyme.

Further, the present invention also provides a cartridge for carrying out the method as described above. The method can be carried out in a particularly efficient manner by using the cartridge.

The cartridge comprises a main body having first and second chambers and a cover member for covering the top openings of the chambers. The cover member is provided with first and second openings or apertures, each of which is adapted for receiving a sample tube, i.e. a filtration column, containing a liquid sample. The first aperture is in communication with the first chamber, and the second aperture is in communication with the second chamber. The cover member is provided with first and second vacuum ports, each of which is adapted for connection with a vacuum source. The first vacuum port is in communication with the first chamber, and the second vacuum port is in communication with the second chamber. The cartridge may be part of a system also comprising one or more vacuum sources, which are or can be selectively coupled to the first and second vacuum ports. Further, the system may comprise a retaining means to which the cartridge can be securely and selectively coupled. The system may also comprise a robotic device which is adapted for automatically pipetting fluids into sample tubes.

In a preferred embodiment a vacuum can be generated in the first chamber when the sample tube is inserted into the first aperture and the or a vacuum source is connected to the first vacuum port. Similarly, a vacuum can be generated in the second chamber when the sample tube is inserted into the second aperture and the or a vacuum source is connected to the second vacuum port.

In a preferred embodiment the first chamber is larger than the second chamber.

In a preferred embodiment the second chamber is formed with a downwardly extending recess which is arranged in alignment with the second aperture and which is sized for accommodating the lower end of the sample tube inserted into the second aperture.

In a preferred embodiment the lower end of the sample tube is provided with a filter matrix, wherein the filter matrix is characterized by a pore size which is sufficiently small to retain microbial cells, in particular bacterial cells, wherein the pore size of the filter matrix is less than 4 µm.

Figure 3:
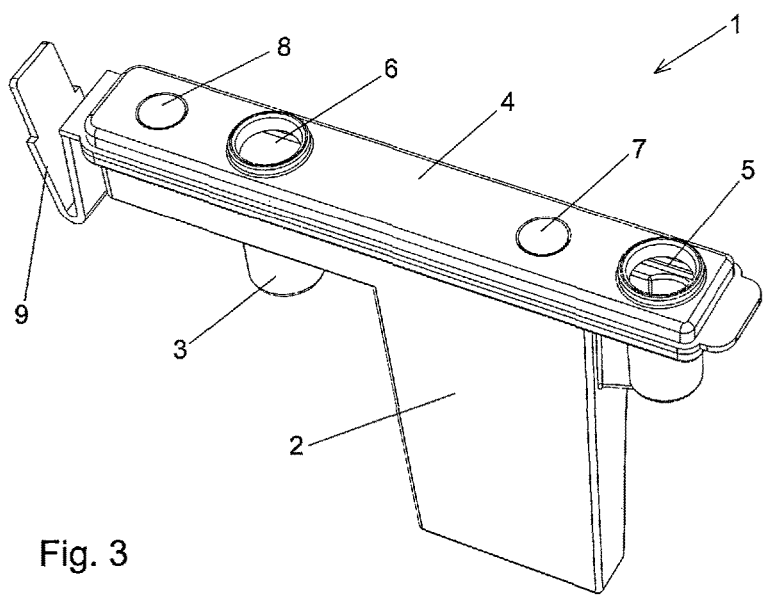
FIG. 3 shows a perspective view of a cartridge for use in a device for enriching and/or isolating nucleic acids from microbial cells.

FIG. 3 shows a perspective view of a cartridge 1 adapted for use in a device for enriching and/or isolating nucleic acids from microbial cells. The cartridge 1 comprises an elongated main body having two separate chambers 2 and 3, and a cover member 4 for covering the top openings of the chambers, wherein the cover member is provided with two apertures 5, 6 for receiving a sample tube (e.g. spin column) which contains the liquid sample, wherein the apertures are each in communication with a corresponding one of the two chambers. Further, the cover member 4 is formed with two vacuum ports 7, 8 each adapted for connection with a suitable vacuum means, wherein the vacuum ports are also in communication with a corresponding one of the two chambers. Finally, one end of the cover 4 or the main body of the cartridge can be provided with engagement means 9 for engaging the cartridge 1 with the device (not shown).

Figure 4:
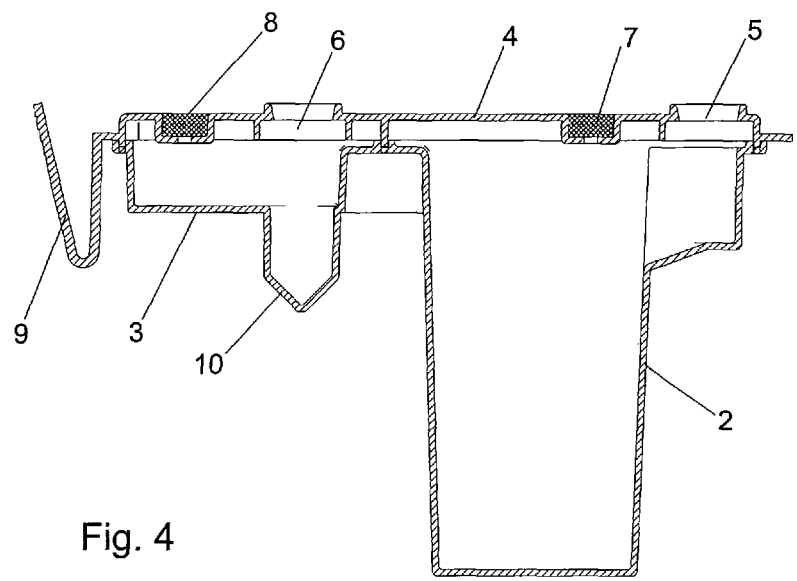
FIG. 4 shows a cross-sectional view of the cartridge of FIG. 3.

FIG. 4 shows a cross-sectional view of the cartridge of FIG. 3. As shown, the two chambers 2 and 3 include a first large chamber 2 and a second small chamber 3 which are separated from each other. For example, the cover member 4 is formed with sealing means for sealingly separating the two chambers, and for sealingly connecting the cover member with the main body. It is obvious from FIG. 4 that the first aperture 5 is in communication with the first chamber 2, and that the second aperture 6 is in communication with the second chamber 3. Both apertures 5, 6 have an inner diameter which substantially corresponds to the outer diameter of the sample tube. The diameter of the sample tube decreases from the open upper end thereof towards the lower end which is provided with a filter membrane. Thus, the apertures 5, 6 are suitable for receiving and supporting the sample tube when the sample tube is inserted into the respective aperture. Advantageously, the apertures 5, 6 are provided with sealing means for sealingly contacting the outer circumferential wall of the sample tube when the sample tube is inserted into the respective aperture.

It is further obvious that the first chamber 2 is much larger than the second chamber 3. The second chamber 3 is formed with a downwardly extending recess 10 which is arranged in alignment with the second aperture 6 and sized for accommodating the lower end of the sample tube when said sample tube is inserted into the second aperture 6.

Figure 5:
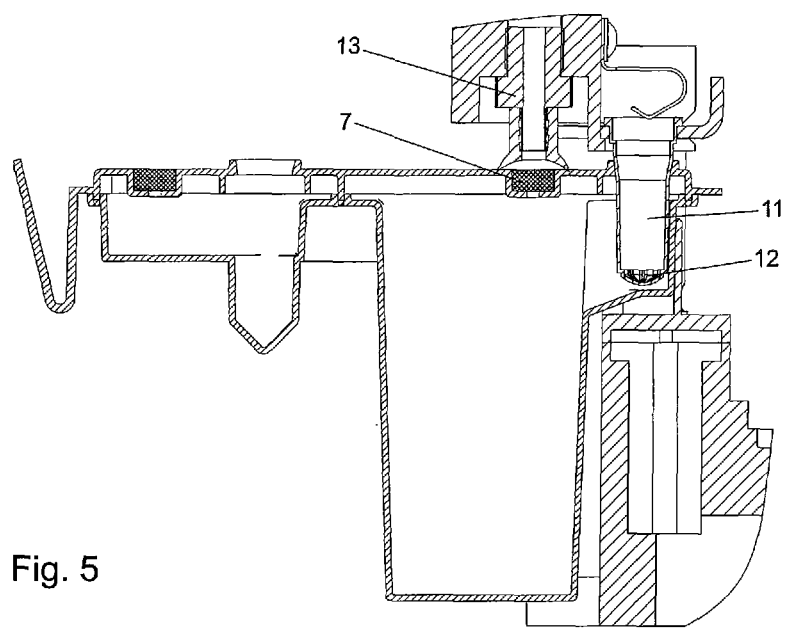
FIG. 5 shows the cartridge of FIG. 4 together with components of the device for enriching and/or isolating nucleic acids from microbial cells in a configuration for conducting the filtration and subsequent lysis, washing and nucleic acid binding.

FIG. 5 shows the cartridge of FIG. 4 together with components of the device for enriching and/or isolating nucleic acids from microbial cells in a configuration for conducting the filtration and washing steps during nucleic acid isolation. In this configuration, the sample tube 11 which contains the microbial cells is inserted into the first aperture 5 which is in communication with the first large chamber 2. As previously described, the outer circumferential surface of the sample tube is in sealed contact with the inner edge of the first aperture 5. As the sample tube 11 has a somewhat conical shape, there is a strong contact between the first aperture and the sample tube. Preferably, a lead spring or a similar retaining means is provided for increasing the engagement force between the sample tube and the first aperture of the cartridge. The lower end of the sample tube 11 is provided with a filter matrix 12 (e.g. a filter membrane) which preferably comprises or consists of silica or glass. The filter matrix is characterized by a pore size which is sufficiently small to retain microbial cells, in particular bacterial cells, i.e. the bacterial cells are collected on the filter matrix of the sample tube while the liquid of the sample and all components dissolved therein pass through the filter matrix 12 and enter into the large chamber 2. For effectively retaining microbial cells, it is preferred that the pore size of the filter matrix is less than 4 µm, less than 3 µm, less than 2 µm, less than 1 µm, less than 0.5 µm, or less than 0.25 µm. Commonly used filter materials used for sterile filtration in the pharmaceutical and food industry have a pore size of 0.22 µm. Accordingly, a pore size of 0.22 µm or below, such as 0.2 µm, can also be used in the methods of the invention. As described above, the filtration and washing steps can be assisted by a vacuum generated in the first large chamber 2. In other words, the filtration and washing steps will be driven by a reduced pressure on one side of the filter matrix, e.g. by using a vacuum device. Preferably, the vacuum is generated in the first large chamber by means of a vacuum pump with is coupled—via a vacuum pipe 13—to the first vacuum port 7 which is in communication with the first large chamber 2. As shown in FIG. 5, the vacuum pipe 13 is preferably provided with a rubber seal to enhance the sealed contact between the lower end of the vacuum pipe and the vacuum port 7. It is preferred that the vacuum port 7 is provided with filter means to prevent that foreign material may enter the large chamber. After completion of the filtration step, the microbial cells that were originally present in the liquid sample are located on the surface of or within the pores of the filter matrix, and the reagent passed through the filter matrix is collected in the first large chamber. The cells will then be lysed on the filter matrix, e.g. by the addition of a solution that contains an enzyme which breaks down the microbial cell wall. The solution is added to the filter matrix and the matrix is soaked with the solution by a short pulse of vacuum. Optionally, a proteinase solution is then added, and the matrix is soaked with the solution by a short pulse of vacuum. The matrix is then washed and the nucleic acids are bound to the matrix by the addition of a solution of a chaotropic salt, as described in the below Example 3 (see phase 3 of the method).

Figure 6:
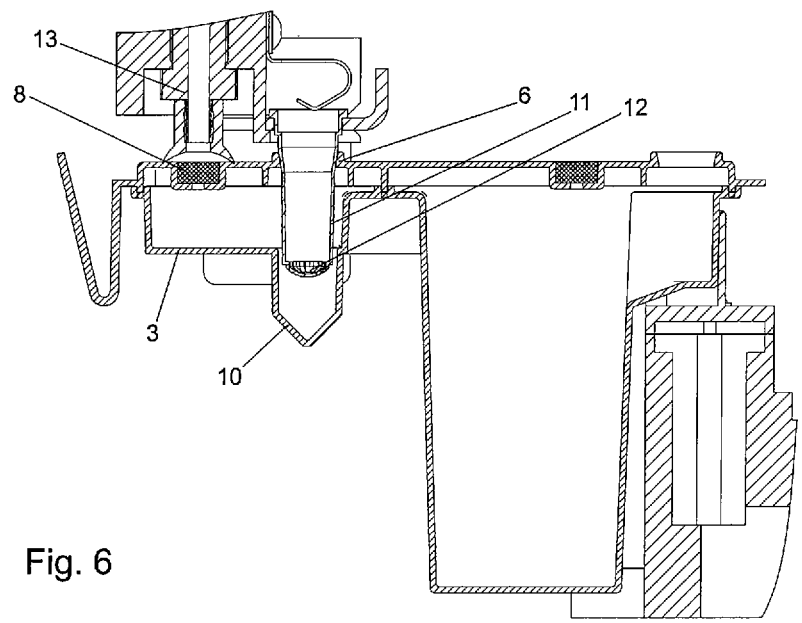
FIG. 6 shows the cartridge together with components of the device for enriching and/or isolating nucleic acids from microbial cells of FIG. 5 in a configuration for conducting the elution step.
Figure 7:
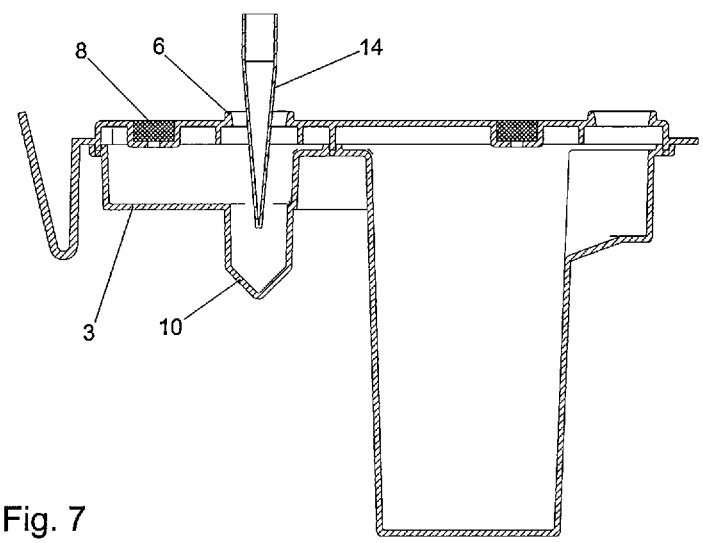
FIG. 7 shows the cartridge of FIG. 4 at the final method step of the invention, where a pipette 14 is inserted into the second aperture 6 for removing the liquid from the recess 10 of the second chamber 3.

FIG. 6 shows the cartridge together with components of the device for enriching and/or isolating nucleic acids from microbial cells in a configuration for conducting the elution step. Before conducting the elution step, the sample tube 11 is removed from the first aperture 5. At the same time, the vacuum pipe 13 is disengaged from the vacuum port 7. Thereafter, the sample tube 11 and the vacuum pipe 13 are displaced, and the sample tube 11 is inserted into the second aperture 6 which is in communication with the second small chamber 3 of the cartridge 1. At the same time, the vacuum pipe 13 is brought into engagement with the second vacuum port 8 which is also in communication with the second small chamber 3. Thereafter, for conduction of the elution step, a vacuum is generated in the second chamber 3, and the nucleic acids bound to the filter matrix are eluted to recover the nucleic acids. The liquid which is removed from the matrix is collected in the recess 10. In a final step, shown in FIG. 7, the sample tube 11 and the vacuum pipe 13 are removed from the cartridge, and a pipette 14 can be inserted into the second aperture 6 for removing the liquid containing the isolated nucleic acids from the recess 10 of the second chamber 3.

The invention is described in the following on the basis of examples, for the purpose of illustration, without limiting the invention. It will be evident to a person skilled in the art that modifications and variations of the examples described are possible without deviating from the idea of the invention.

EXAMPLES

The following materials were used for the nucleic acid purification tests presented below:
Buffer 1 (0.075 Mol/l Tris-HCl, pH 8.0; 2.5 Mol/l guanidine hydrochloride; 2.5% (vol/vol) Tween-20; 0.15 Mol/l $MgCl_2$; 0.3% (vol/vol) antifoam agent (Hain Lifescience, Nehren, Germany));
Buffer 2 (0.05 Mol/l Tris-HCl, pH 8.0; 0.05 Mol/l EDTA);
Buffer 3 (0.05 Mol/l Tris-HCl, pH 8.0; 0.01 Mol/l EDTA; 20% (wt/vol) sucrose; 0.15% (wt/vol) sodium azide);
Buffer 4 (0.05 Mol/l Tris-HCl, pH 8.0; 0.01 Mol/l EDTA; 0.006 Mol/l $CaCl_2$; 1.3% (weight/vol) SDS);
Buffer 5 (0.125 Mol/l Tris-HCl, pH 8.0; 2.5 Mol/l guanidine isothiocyanate; 2.5% (vol/vol) Tween-20; 0.045 Mol/l $MgCl_2$; 37.5% (vol/vol) 2-propanole);
Buffer 6 (70% (vol/vol) ethanol);
DNA-free water (Molzym, Bremen)
DNAse (MolDNAse, 500 U/µl, Molzym, Bremen, Germany)
Proteinase K (10 mg/mL; Molzym, Bremen, Germany)
BugLysis cell wall degrading reagent (Molzym, Bremen, Germany)
2-mercaptoethanol (Merck, Darmstadt, Germany)

Example 1

Protocol for Isolating Bacterial DNA from a Liquid Sample

This example shows the applicability of the method of the invention for enriching and/or isolating nucleic acids from microbial cells which are present in a liquid sample, e.g. a tab water sample.

Phase 1: Filtration and Lysis of Microorganisms
Filtrate liquid sample, e.g. 1 to 2 mL, by placing a silica or glass membrane spin column (Qiagen, Hilden, Germany) in a vacuum station; pipette 0.6 mL of the sample into the column and apply vacuum until sample has completely passed the membrane; repeat the procedure with the rest of the sample.
Wash spin column with 0.6 mL buffer 2 by vacuum filtration until all buffer is passed through.
Mix 80 µl buffer 3 with 20 µl BugLysis. Add to spin column and apply a short pulse of vacuum to soak the membrane with the liquid.
Incubate at room temperature (20-25° C.) for 30 min.
Mix 150 µl buffer 4 with 20 µl proteinase K. Add to spin column and apply a short pulse of vacuum to soak the membrane with the liquid.
Incubate at room temperature (20-25° C.) for 10 min.
Phase 3: Extraction and Purification
Pipette 500 µl Buffer 5 into the spin column and apply vacuum until all liquid has passed the column.
Pipette 400 µl Buffer 6 into the spin column and apply vacuum for 10 min to dry the membrane.
Pipette 200 µl DNA-free water to the column and incubate for 1 min.
Elute into a DNA-free 1.5 mL Eppendorf tube by applying vacuum for 1 min.

Example 2

Protocol for Isolating Bacterial DNA from a Human Blood Sample

This example shows the applicability of the method of the invention for enriching and/or isolating nucleic acids from microbial cells which are present in a liquid sample that comprises both microbial cells and human blood cells.
Phase 1: Generation of Blood Cell Lysate
Transfer 1 mL fresh whole blood (stabilized with EDTA, heparin or citrate) from a blood collection tube to a 2 mL Eppendorf tube. Add 0.8 mL Buffer 1 and 10 µl MolDNase for human blood cell lysis. Mix the sample by vortexing.
Incubate at 45° C. for 10 min (degradation of free DNA).
Mix with 20 µl proteinase K.
Incubate at 45° C. for 10 min (liquefaction of lysate).
Phase 2: Filtration of Blood Lysate and Lysis of Microorganisms
Filtrate blood lysate by placing a silica or glass membrane spin column (Qiagen, Hilden, Germany) in a vacuum station; pipette 0.6 mL lysate into the column and apply vacuum until lysate has completely passed the membrane; repeat the procedure with the rest of the lysate.
Wash spin column with 0.6 mL buffer 2 by vacuum filtration until all buffer is passed through.
Mix 80 µl buffer 3 with 20 µl BugLysis. Add to spin column and apply a short pulse of vacuum to soak the membrane with the liquid.
Incubate at room temperature (20-25° C.) for 30 min.
Mix 150 µl buffer 4 with 20 µl proteinase K. Add to spin column and apply a short pulse of vacuum to soak the membrane with the liquid.
Incubate at room temperature (20-25° C.) for 10 min.
Phase 3: Extraction and Purification
Pipette 500 µl Buffer 5 into the spin column and apply vacuum until all liquid has passed the column.
Pipette 400 µl Buffer 6 into the spin column and apply vacuum for 10 min to dry the membrane.

Pipette 200 µl DNA-free water to the column and incubate for 1 min.

Elute into a DNA-free 1.5 mL Eppendorf tube by applying vacuum for 1 min.

Example 3

Isolation of DNA from S. aureus $6.8 \times 10^4$ cfu/mL S. aureus were subjected to the protocol of Example 1. DNA was measured in quantitative Real-Time PCR assay (Molzym Mastermix 16S). Standard: centrifugation method (Molzym MolYsis Complete5).

Result: The results are depicted in FIG. 1. It can be seen that the extraction of S. aureus DNA gave threshold values (glass membrane: mean C(t)=20.25; silica membrane: mean C(t)=22.26) which are comparable to standard centrifugation methods (mean C(t)=22.09).

Example 4

Isolation of DNA from S. aureus

Various loads of S. aureus were subjected to the protocol of Example 1. DNA was measured in quantitative Real-Time PCR assay (Molzym Mastermix 16S). Standard: centrifugation method (Molzym MolYsis Complete5).

Figure 2:
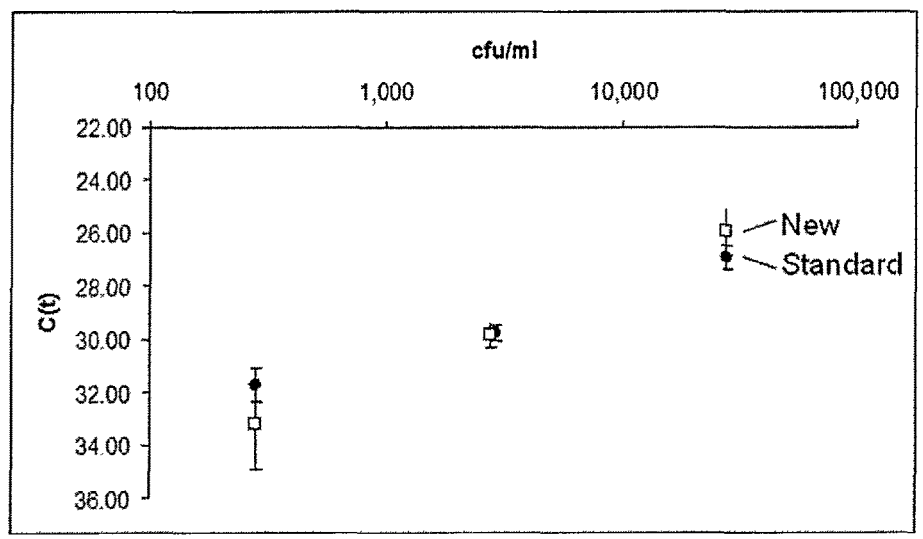
FIG. 2 shows the extraction of *S. aureus* at various loads by the method of the invention. DNA was measured in a quantitative Real-Time PCR assay (Molzym Mastermix 16S). Standard: centrifugation method (Molzym MolYsis Complete5).

Result: The results are depicted in FIG. 2. As depicted in the figure, the DNA recoveries obtained by the method of protocol 1 were comparable to standard centrifugation methods at all loads tested. Thus, DNA extraction by the new method is as efficient for S. aureus as the standard methods.

Example 5

Isolation of DNA from E. coli

Various loads of immobilized E. coli were subjected to the protocol of Example 1. DNA was measured in quantitative Real-Time PCR assay (Molzym Mastermix 16S). Standard: centrifugation method (Molzym MolYsis Complete5).

Result: The results are shown in Table 1. Extraction of DNA from a dilution series of E. coli gave threshold values comparable with standard centrifugation methods. Specific peaks were observed in the melt curve analyses using extracts obtained by the method of protocol 1, whereas specific peaks appeared only with 6,000 and 600 cfu/mL E. coli by the standard method. Thus, for E. coli DNA, the method of the invention is at least as efficient as the standard method.

TABLE 1

| | Threshold (C(t))/ Specific peak ($T_m$ = 88.8-89.2° C.) | |
| --- | --- | --- |
| E. coli titre | New method | Standard method |
| 6000 cfu/mL | 29.06/yes | 27.16/yes |
| 600 cfu/mL | 31.64/yes | 31.68/yes |
| 60 cfu/mL | 33.05/yes | 31.72/no |

Example 6

Isolation of DNA from Different Bacteria in Mock Blood Samples

The limits of detection (mean value from 2 experiments) of microorganisms in mock blood samples extracted according to protocol 2 was measured. DNA was measured in quantitative Real-Time PCR assay (Molzym Mastermix 16S). Standard: centrifugation method (Molzym MolYsis Complete5).

Result: The results are shown in Table 2. It can be seen that the new method supplies DNA from microorganisms at quantities that correspond to microbial loads prevalent in septicemic blood (1 to >100 cfu/mL).

TABLE 2

| Strain | Limit of detection (cfu/mL) | Threshold C (t) | Specific peak |
| --- | --- | --- | --- |
| Staphylococcus aureus | <100 | 37.91 | + |
| Escherichia coli | <100 | 33.47 | + |
| Streptococcus agalactiae | <100 | 37.00 | + |
| Candida albicans | <20 | 34.39 | + |

Example 7

Limits of Detection of Microorganisms in Dependence of the Blood Volume

The limits of detection (mean of 3 experiments) of different bacterial microorganisms in dependence of the blood volume extracted according to the protocol of Example 2 were determined.

Result: The results are shown in Table 3. It can be seen there that the limit of detection of two common pathogenic strains could be further decreased by increasing the blood volume analyzed.

TABLE 3

| Microorganism | Blood volume (mL) | Titer (cfu/mL) | Specific peak |
| --- | --- | --- | --- |
| Staphylococcus aureus | 1 | 60 | + |
| | 2 | 30 | + |
| | 5 | 12 | + |
| | 10 | 6 | + |
| Escherichia coli | 1 | 120 | + |
| | 2 | 60 | + |
| | 5 | 24 | + |
| | 10 | 12 | + |

The invention claimed is:

1. Method for enriching and/or isolating nucleic acids from microbial cells, comprising
    (a) filtering a liquid sample comprising microbial cells through a nucleic acid-binding matrix, which has a pore size small enough to retain the microbial cells;
    (b) lysing the microbial cells on the matrix to release the nucleic acids from the microbial cells, wherein said lysing does not involve precipitation of the nucleic acids released from the microbial cells;
    (c) optionally, degrading proteins on the matrix by the addition of an enzyme having proteinase activity;
    (d) binding the nucleic acids to the matrix by the addition of monovalent or multivalent cations;
    (e) optionally, washing the matrix to remove any unbound material; and
    (f) eluting the nucleic acids.

2. Method according to claim 1, wherein the matrix has a pore size of less than 4 µm.

3. Method according to claim 1, wherein the filtration in step (a) is carried out either by centrifugation or by use of a vacuum device.

4. Method according to claim 1, wherein the cell wall degrading enzyme in step (b) is lysozyme, lysostaphin, or mutanolysin.

5. Method according to claim 1, wherein the enzyme having proteinase activity in step (c) is proteinase K.

6. Method according to claim 1, wherein said monovalent and/or multivalent cations in step (d) are selected from the group consisting of $Na^+$, $Ca^{2+}$, $Mg^{2+}$, $NH^{4+}$, and $Al^{2+}$.

7. Method according to claim 6, wherein said monovalent cations in step (d) are derived from a chaotropic salt.

8. Method according to claim 1, wherein a washing buffer is used in step (e) which comprises at least 50% (vol/vol) alcohol.

9. The method of claim 1, wherein said liquid sample in step (a) comprises both microbial cells and higher eukaryotic cells and/or tissues, said method further comprising:

lysing the higher eukaryotic cells and/or tissues in the sample under conditions which do not result in the lysis of the microbial cells;

degrading nucleic acids released from the eukaryotic cells and/or tissues by the addition of an enzyme having nuclease activity; and optionally, degrading proteins released from the eukaryotic cells and/or tissues by the addition of an enzyme having proteinase activity;

before filtering said liquid sample through said nucleic-acid binding matrix in step (a).

10. The method of claim 9, wherein the higher eukaryotic cells are blood cells or tissue cells of human or animal origin.

11. Method according to claim 9, wherein said enzyme having nuclease activity is a DNA-degrading nuclease.

12. Method according to claim 7, wherein the chaotropic salt is selected from the group consisting of guanidine hydrochloride, sodium iodide, guanidine isothiocyanate, and mixtures thereof.

13. Method according to claim 11, wherein the DNA-degrading nuclease is active under chaotropic conditions.

14. Method according to claim 1, wherein said nucleic acid-binding matrix is a silica or glass matrix.

15. Method according to claim 1, wherein said microbial cells are bacterial cells.

* * * * *